United States Patent [19]
Dhingra et al.

[11] Patent Number: 6,048,887
[45] Date of Patent: Apr. 11, 2000

[54] SUBSTITUTED PYRROLES

[75] Inventors: Urvashi Hooda Dhingra, Nutley; Donna Mary Huryn, Allentown; June Ke, Montclair; Giuseppe Federico Weber, Cedar Grove, all of N.J.

[73] Assignee: Hoffmann-La Roche Inc., Nutley, N.J.

[21] Appl. No.: 09/268,887

[22] Filed: Mar. 16, 1999

Related U.S. Application Data

[60] Provisional application No. 60/078,331, Mar. 17, 1998.

[51] Int. Cl.$^7$ ...................... A61K 31/405; C07D 209/08
[52] U.S. Cl. ............................................. 514/414; 548/455
[58] Field of Search ............................... 548/455; 514/414

[56] References Cited

U.S. PATENT DOCUMENTS

| | | | |
|---|---|---|---|
| 5,057,614 | 10/1991 | Davis et al. | 548/466 |
| 5,380,746 | 1/1995 | Barth et al. | 514/414 |

FOREIGN PATENT DOCUMENTS

| | | |
|---|---|---|
| 0 328 026 | 8/1989 | European Pat. Off. . |
| WO 98/04551 | 2/1998 | WIPO . |
| WO 98/04552 | 2/1998 | WIPO . |
| WO 98/04553 | 2/1998 | WIPO . |

OTHER PUBLICATIONS

Jackson B. Hester, J. Org. Chem., vol. 29, pp. 1158–1160 (1964).

Peter D. Davis et al., Journal of Medicinal Chemistry, vol. 35, No. 1, p. 177–184 (1992).

*Primary Examiner*—Joseph McKane
*Attorney, Agent, or Firm*—George W. Johnston; Patricia S. Rocha-Tramaloni

[57] ABSTRACT

Certain substituted pyrroles are antiproliferative agents useful in the treatment of cancer.

11 Claims, No Drawings

SUBSTITUTED PYRROLES

Provisional application no 60/078,331 filed on Mar. 17, 1998.

BRIEF SUMMARY OF THE INVENTION

The invention relates to certain specific substituted pyrroles. More particularly, this invention is directed to substituted pyrroles having the following formulas:

I

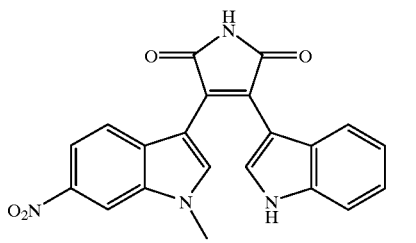

II

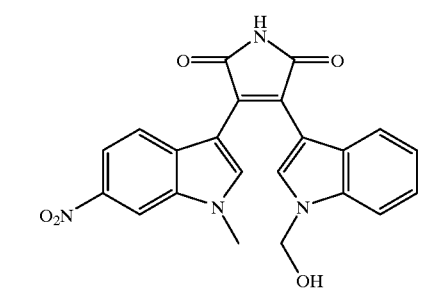

III

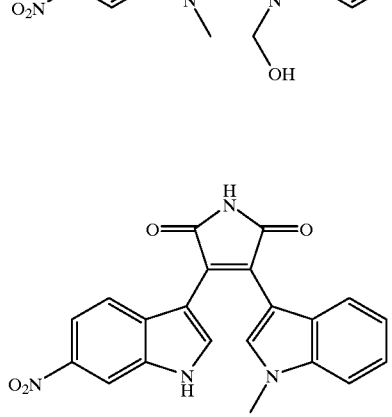

The foregoing compounds and their pharmaceutically acceptable salts, and prodrugs of said compounds are antiproliferative agents useful in the treatment or control of cancer, particularly in the treatment or control of solid tumors. The compounds of the invention are especially useful in the treatment or control of breast and colon tumors.

DETAILED DESCRIPTION OF THE INVENTION

The invention relates to substituted pyrroles. Specifically, the invention relates to the following substituted pyrroles

I

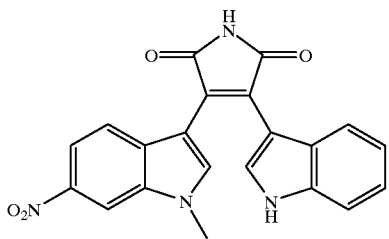

II

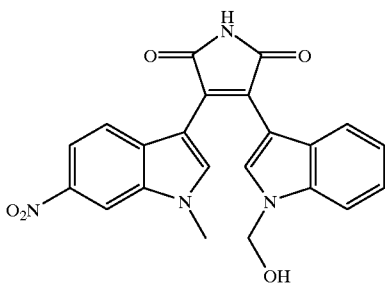

III

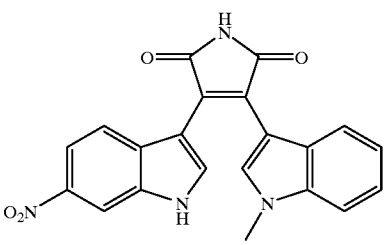

as well as pharmaceutically acceptable prodrugs or pharmaceutically acceptable salts of compounds of formulas I–III.

The compounds of formulas I–III have antiproliferative activity, specifically, they inhibit cell division in G2/M phase of the cell cycle and are generally referred to as "G2/M phase cell-cycle" inhibitors.

The compounds of formulas I–III are similar in structure to and are therapeutically active metabolites of a compound within U.S. Pat. No. 5,057,614.

The term "pharmaceutically acceptable prodrugs" means a compound that may be converted under physiological conditions or by solvolysis to any of the compounds of the formulas I–III or to a pharmaceutically acceptable salt of said compounds.

The compounds of formulas I–III, as well as pharmaceutically acceptable salts of said compounds, are prepared by the following Schemes. The synthesis of each of these compounds is also described in Examples 1–3.

SCHEME 1
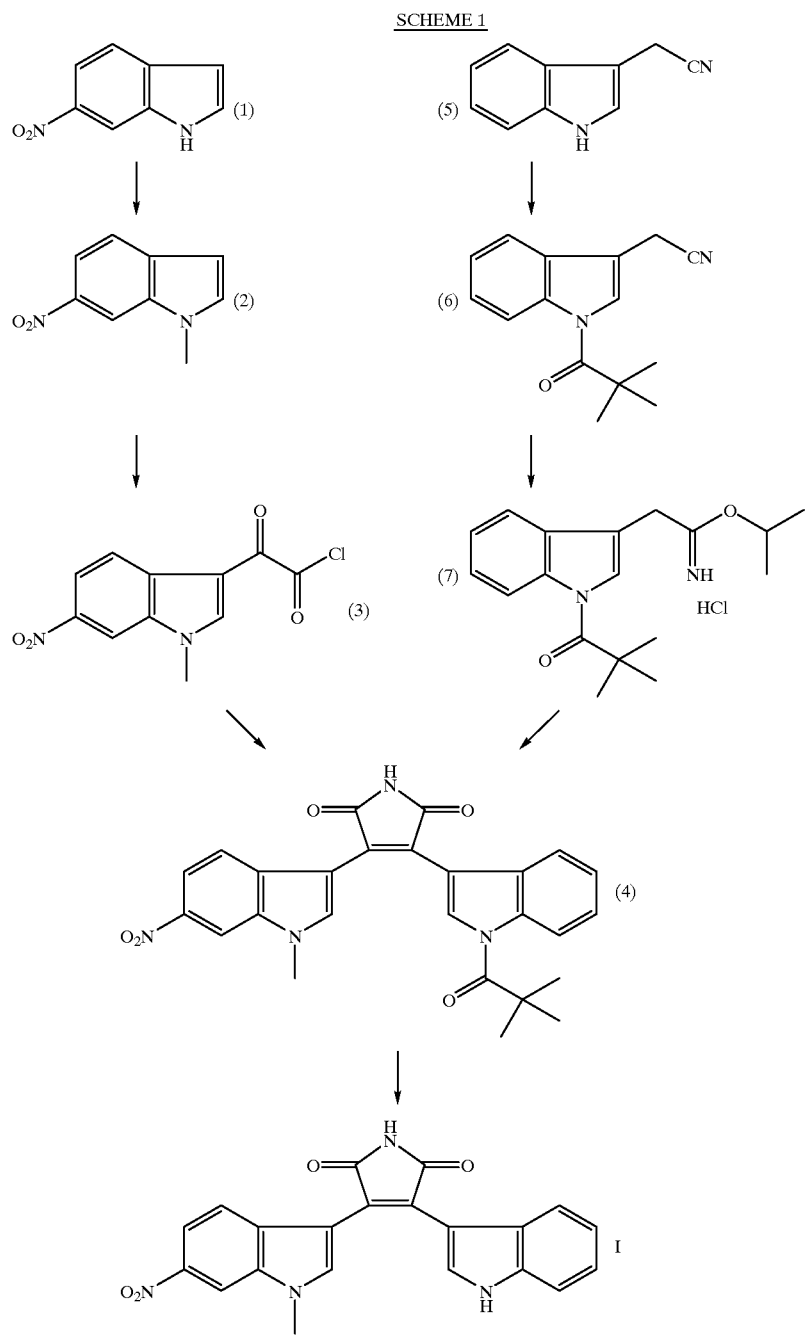

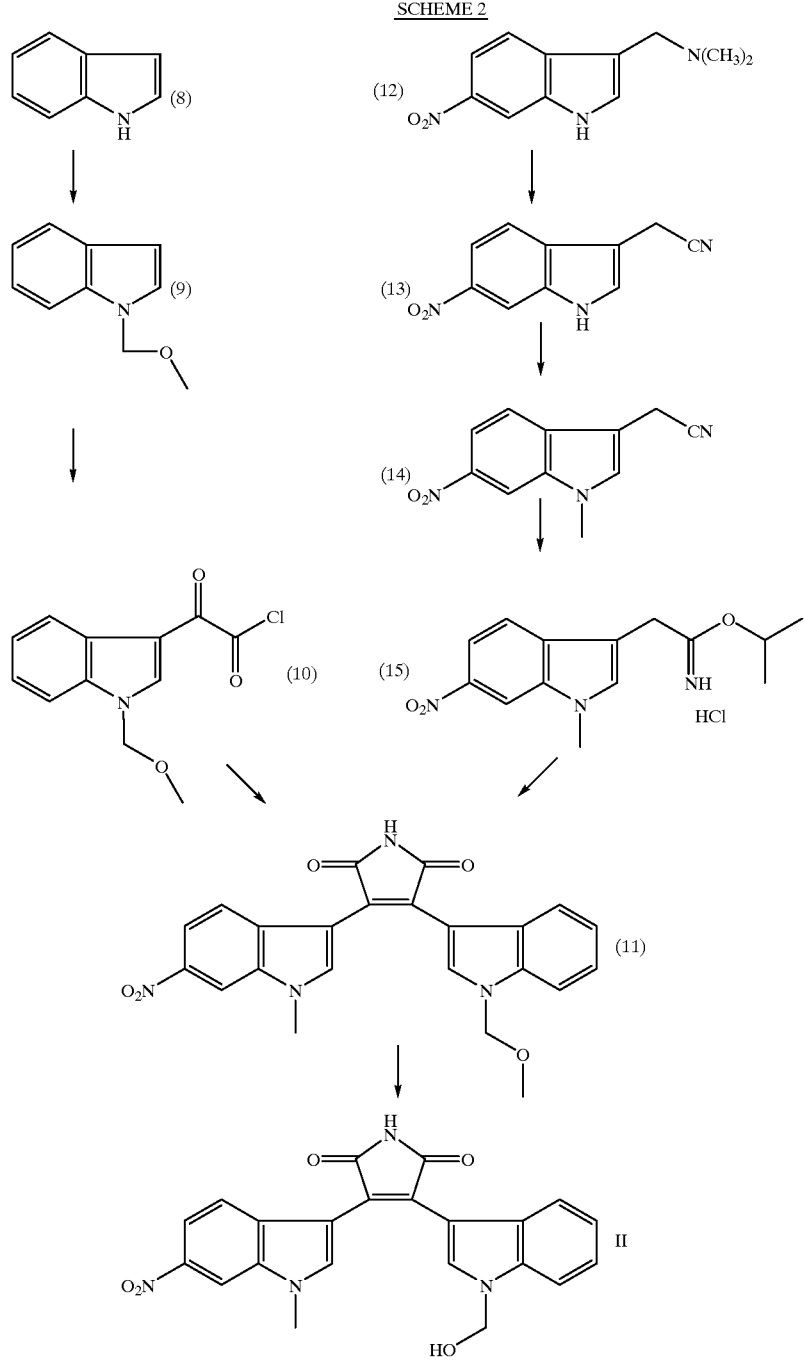

SCHEME 3
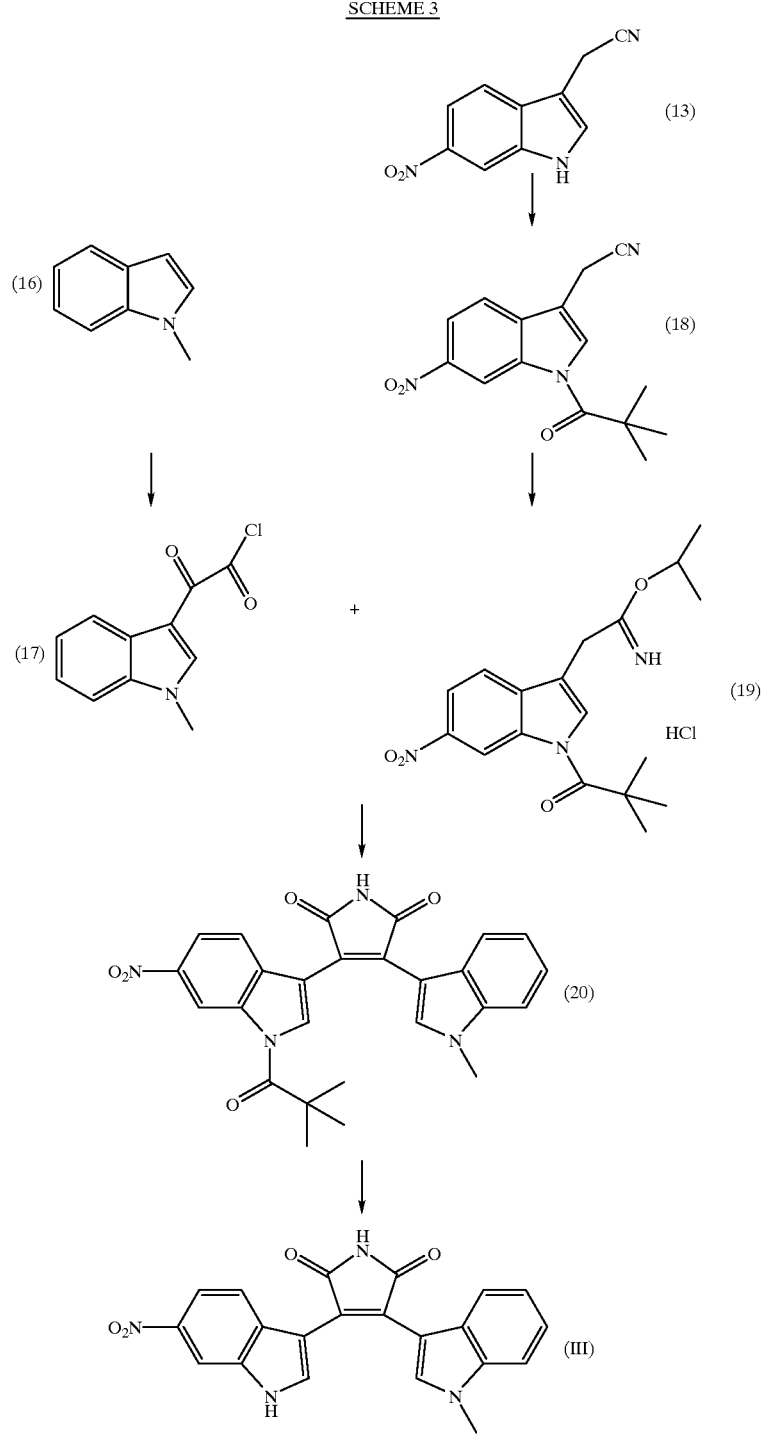

SCHEME 3A

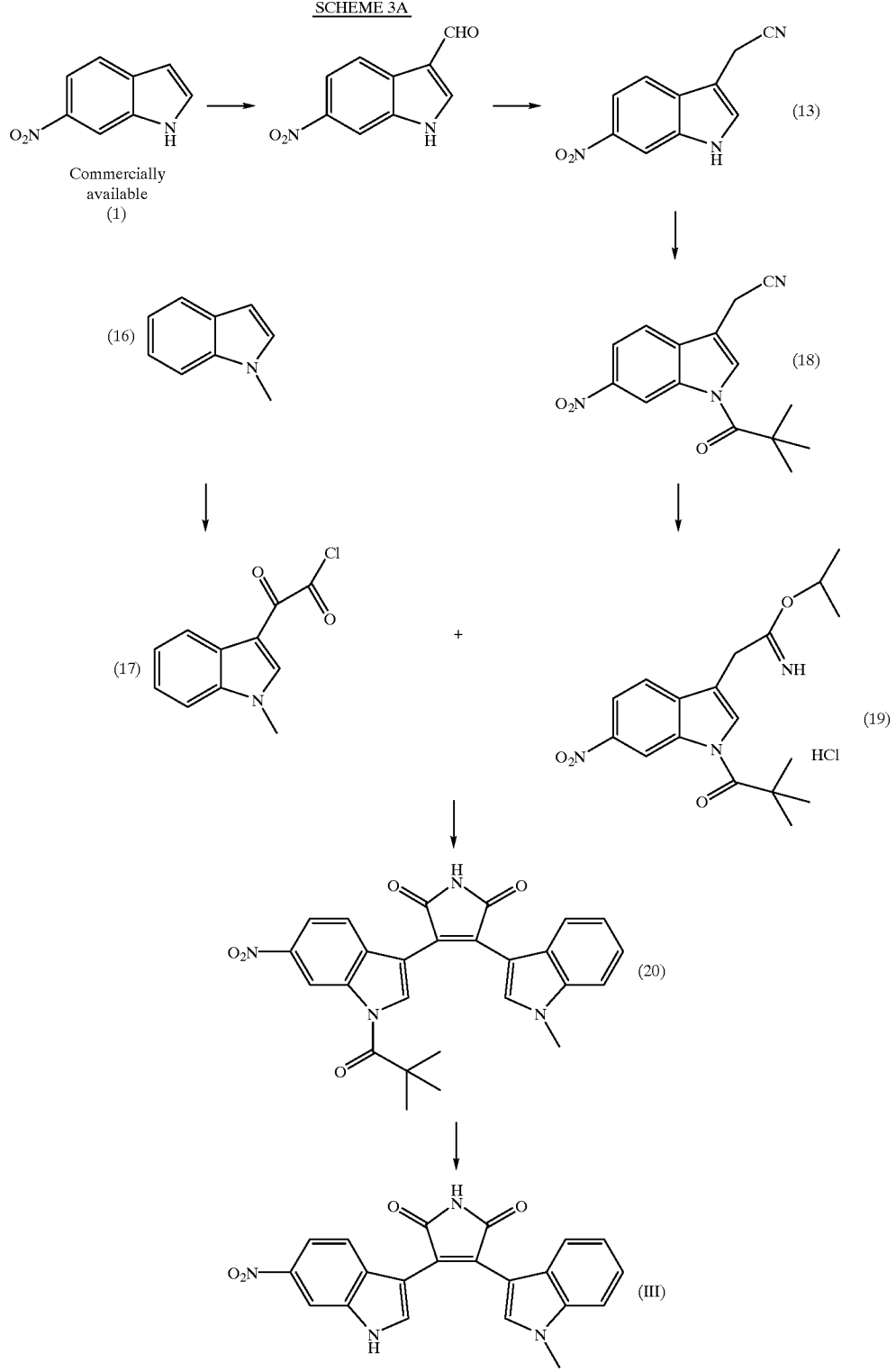

The antiproliferative activity of the compounds of the invention is demonstrated below. These effects indicate that the compounds are useful in treating cancer, in particular solid tumors.

The estrogen receptor negative epithelial breast carcinoma line (MDA-MB-435) was purchased from American Type Cell Culture Collection (ATCC; Rockville, Md.) and was grown in the medium recommended by ATCC. For analysis of the effect of the test compounds on growth of these cells, the cells were plated at 2000 cells per well in a 96-well tissue culture plate ("test plate"), and were incubated overnight at 37° C. with 5% $CO_2$. The next day, the test compounds were dissolved in 100% dimethyl sulfoxide (DMSO) to yield a 10 mM stock solution. Each compound was diluted with sterile distilled water to 1 mM and then was added to triplicate wells of a 96-well "master plate" containing medium in a sufficient quantity to yield a final concentration of 40 µM. The compounds were serially diluted in medium in the "master plate." One-fourth final volume of the diluted compounds was transferred to duplicate "test plates." DMSO was added to a row of "control cells" such that; the final concentration of DMSO in each well was 0.1%. The "test plates" were returned to the incubator, and 3 days post addition of test compound, one "test plate" was analyzed as described below. Similarly, 5 days after addition of test compound, the second "test plate" also was analyzed as described below.

3-(4,5-dimethylthiazole-2-yl)-2,5-diphenyl-2H-tetrazolium bromide (thiazolyl blue; MTT) was added to each well to yield a final concentration of 1 mg/ml. The plate was then incubated at 37° C. for 3 hours. The MTT-containing medium was then removed and 50 µl 100% ethanol was added to each well to dissolve the resulting formazan metabolite. To ensure complete dissolution, plates were shaken for 15 minutes at room temperature. Absorbencies were read in a microtiter plate reader (Molecular Dynamics) at a wavelength of 570 nm with a 650 nm reference. Percent inhibition was calculated by subtracting the blank from all wells, then subtracting the division of the average absorbance of each test triplicate by the average of the controls from 1.00. Inhibitory concentrations ($IC_{50}$ and $IC_{90}$) were determined from the linear regression of a plot of the logarithm of the concentration versus the percent inhibition.

The colon adenocarcinoma line SW480 and the colon carcinoma line HCT-116 also were obtained from the ATCC and were tested according to the same protocol provided above with the following modifications. Cell line SW480 was plated at 1000 cells per well and analyzed at 6 days post addition of the test compound. Cell line HCT-116 was plated at 750 cells per well and analyzed at 4 days post addition of test compound. For the MTT analysis, plates were centrifuged at 1000 rpm for 5 minutes prior to aspiration of the MTT-containing medium, and 100 µl 100% ethanol was used to dissolve the formazan.

The results of the foregoing in vitro tests are set forth below in Tables I–III.

TABLE I

Antiproliferative Activity In Cell Line MDA-MB-435

| Compound | $IC_{50}$ (µM) |
| --- | --- |
| Compound I | 0.03* |
| Compound II | 0.05* |
| Compound III | 0.6* |

*An average of at least three separate experiments.

TABLE II

Antiproliferative Activity In Cell Line HCT-116

| Compound | $IC_{50}$ (µM) |
| --- | --- |
| Compound I | 0.17* |
| Compound II | 0.23* |
| Compound III | 1.66* |

*An average of at least three separate experiments.

TABLE III

Antiproliferative Activity In Cell Line SW480

| Compound | $IC_{50}$ (µM) |
| --- | --- |
| Compound I | 0.20* |
| Compound II | 0.22* |
| Compound III | 1.86* |

*An average of at least three separate experiments.

For analysis of the effect of the compounds on cell cycle progression, MDA-MB-435 cells (ATCC; Rockville, Md.) were plated at $1 \times 10^6$ cells/10 mls per 10 cm dish in the following growth medium: RPMI 1640+10% Heat-Inactivated Fetal Bovine Serum, 2 mM L-glutamine and 50 U/ml pen-strep (all from GIBCO/BRL, Gaithersburg, Md.). The cells were incubated overnight at 37° C. with 5% $CO_2$. The next day, 10 µl of each of the compounds to be tested, in a 100% DMSO solution, was added to individual dishes to obtain /1000× final concentration of the stock solution. In addition, 10 µl 100% DMSO was added to a control dish. The final concentration of DMSO in all plates, including the control, was 0.1%. The plates were returned to the incubator.

Thereafter, at various periods of time, the medium in each plate was removed to a 50 ml centrifuge tube. The cell layer remaining in the dish was then washed with 5 ml of phosphate buffered saline (PBS; GIBCO/BRL). The PBS was removed and combined with the medium in the appropriate tube. The cells were trypsinized for 5 minutes at 37° C., and the solution was collected and combined with the medium and PBS in the appropriate tubes. The tubes were then centrifuged for 5 minutes at 1200 rpm. The cells were fixed by removing the supernatant, tapping the tube to distribute the pellet, then adding 5 mls of cold 70% ethanol while vortexing gently. The cells were then stored at −20° C. for >24 hours.

The cell-containing tubes were taken out of freezer and allowed to sit at room temperature for 20–30 minutes. The tubes were centrifuged at 3000 rpm for 5 minutes. The supernatant was removed, the pellets were washed with 5 ml PBS, and the tubes were centrifuged as above. Subsequently, the supernatant was removed, and the pellet was resuspended in 0.5 ml PBS. Thereafter, 0.5 ml RNAse A (1 mg/ml in PBS) was added to each tube, and the tubes were incubated at 37° C. for 15 minutes. 100 µl propidium iodide (Sigma, St. Louis, Mo.) (1 mg/ml in PBS) was added to each tube, and the tubes were then incubated at room temperature for 2–3 minutes. Each resulting solution was passed through a filter cap tube (Becton Dickinson, San Jose, Calif., #2235).

Samples were read in a FACSort machine (Becton-Dickinson) using the manufacturer's CellQUEST program, and analyzed with the manufacturer is ModFIT software. This measurement provides an indication of the percent of cells in each of the following phases: G0/G1, DNA synthesis (S) and G2/M phases.

The results of a cell cycle progression experiment analyzed at day 1 post addition of test compounds I, II and III are summarized below in Table IV.

TABLE IV

Effect Of Test Compounds On Cell Cycle

| | | % Of Cells In Each Cell Cycle Phase | | |
|---|---|---|---|---|
| Compound | Concentration | G1 | S | G2/M |
| DMSO | 0.1% | 43.93% | 41.08% | 14.99% |
| Compound I | 0.1 μM | 8.27% | 25.21% | 66.52% |
| Compound I | 0.03 μM | 45.30% | 34.67% | 20.03% |
| Compound I | 0.01 μM | 44.95% | 41.04% | 14.00% |
| Compound II | 0.3 μM | 1.11% | 24.99% | 73.90% |
| Compound II | 0.1 μM | 15.54% | 24.06% | 60.40% |
| Compound II | 0.03 μM | 45.45% | 38.06% | 16.50% |
| Compound III | 10 μM | 10.41% | 35.25% | 54.34% |
| Compound III | 3 μM | 3.26% | 48.75% | 47.99% |
| Compound III | 1 μM | 27.21% | 30.19% | 42.60% |

The results summarized in Tables I–IV above demonstrate that compound I, II and III have antiproliferative activity; specifically, they cause an accumulation of cells in the G2/m phase of the cell cycle.

The pyrroles of formulas I–III above and their aforementioned salts can be used as medicaments, for example, in the form of pharmaceutical preparations, which can be administered orally, for example, in the form of tablets, coated tablets, dragees, hard or soft gelatin capsules, solutions, emulsions or suspensions. They can also be administered rectally, for example, in the form of suppositories or parenterally, for example, in the form of injection solutions.

For the manufacture of pharmaceutical preparations these compounds can be formulated with therapeutically inert, inorganic or organic carriers. Lactose, maize starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid polyols. Depending on the nature of the active substance no carriers are, however, generally required in the case of soft gelatin capsules. Suitable carriers for the manufacture of solutions and syrups are, water, polyols, saccharose, invert sugar and glucose. Suitable carriers for injection are water, alcohols, polyols, glycerine, vegetable oils, phospholipids and surfactants, suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, the pyrroles of formulas I–III and their aforementioned salts can be used in the treatment or control of oncological disorders. The dosage can vary within wide limits and will, of course, be adjusted to the individual requirements in each particular case. In general, in the case of oral or parenteral administration to adult humans weighing about 70 kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The following Examples illustrate the present invention.

EXAMPLE 1

Preparation of 3-(1H-indol-3-yl]-4-(1-methyl-6-nitro-1H-indol-3 -yl)-pyrrole-2,5-dione(I)

A. 1-Methyl-6-nitro-1H-indole (2)

To a slurry of 0.33 g (8.3 mmol) of NaH (60% dispersion in oil) in 30 ml of dried dimethylformamide ("DMF"), was added 0.973 g (6.00 mmol) of commercially available (Lancaster, Windham, N.H.) 6-nitro-IH-indole (1) at 0–5° C. over a period of 10 minutes. After 1 hour stirring at the same temperature, 0.75 ml (12.1 mmol) of methyl iodide was added and the mixture was stirred at the same temperature for 30 minutes, then at room temperature for 1 hour, poured into ice and water and extracted with ethyl acetate. The organic phase was washed with brine, dried over $MgSO_4$, and concentrated to yield 0.814 g (77.5%) of 1-methyl-6-nitro-1H-indole (2) as a yellow solid. This material was used without purification.

B. (1-Methyl-6-nitro-1H-indol-3-yl)-oxo-acetyl chloride (3)

To a solution of 1.33 g (7.55 mmol) of 1-methyl-6-nitro-1H-indole (2) in 40 ml of ether were added 1.5 ml (17.2 mmol) of oxalyl chloride at 0–5° C. under Argon. A precipitate was formed. After 3 hours stirring, the resulting solid was filtered, washed with a small amount of ether and dried to yield 1.9 g (95%) of (1-methyl-6-nitro-1H-indol-3-yl)-oxo-acetyl chloride (3) as a yellow solid. This material was used without purification.

C. [1-(2,2-Dimethyl-propionyl)-1H-indol-3-yl]-acetonitrile (6)

Using the procedure of subpart A above, the N-alkylation reaction of 10.2 g (65 mmol) of commercially available (1H-indol-3-yl)-acetonitrile (5) (1H-indol-3-yl)-acetonitrile (Acros Organics, Belgium) with 8.7 ml (71 mmol) of trimethylacetyl chloride and 3.4 g (85 mmol) of NaH (60% dispersion in oil) as a base in 115 ml of DMF yielded 6.6 g (38.7%) of [1-(2,2-dimethyl-propionyl)-1H-indol-3-yl]-acetonitrile (6) as a yellow oil after chromatographic purification.

D. [1-(2,2-Dimethyl-propionyl)-1H-indol-3yl]-3-ethyanimidic acid 1-methylethylester hydrochloride (7)

To a slurry of 6.6 g (27.5 mmol) of [1-(2,2-dimethyl-propionyl)-1H-indol-3-yl]-acetonitrile (6) from Step C above in 105 ml of 2-propanol, 40 ml (0.563 mol) of acetyl chloride was added dropwise at 0–5° C. over a 20 minute period. The reaction mixture was stirred at room temperature overnight, concentrated and the residue was diluted with approximately 75 ml of ethyl acetate, heated for 15 minutes on a steam bath, cooled and placed in a freezer. The precipitate was filtered and dried to yield 6.0 g (65.0%) of [1-(2,2-dimethyl-propionyl)-1H-indol-3-yl]-3-ethanimidic acid 1-methylethylester hydrochloride (7) as a white solid.

E. 3-[1-(2,2-Dimethyl-propionyl)-1H-indol-3-yl]-4-(1-methyl-6-nitro 1H -indol-3-pyrrole-2,5-dione (4)

To a solution of 1.25 g (4.69 mmol) of (1-methyl-6-nitro-1H-indol-3-yl)-oxo-acetyl chloride (3) from Step B above and 1.6 g (4.75 mmol) of [1-(2,2-dimethyl-propionyl)-1H-indol-3-yl]-3-ethanimidic acid 1-methyl ethylester hydrochloride (7) from Step D above in 80 ml of methylene chloride was added 2.6 ml (18.65 mmol) of triethylamine at 0° C. and under Argon. After stirring at the same temperature for 30 minutes, the reaction mixture was then stirred at room temperature for 3 ½ hours and diluted with more methylene chloride. The organic phase was washed with water, 0.5N-HCI solution, brine, dried over $MgSO_4$ and concentrated to give 3.01 g of a foam. This material was dissolved in 50 ml of toluene and treated with 987.9 mg (5.19 mmol) of p-toluenesulfonic acid at 0° C. After 3 hours stirring at room temperature the reaction mixture was extracted with methylene chloride. The organic phase was washed with a saturated NaHCO$_3$ solution, brine, dried over MgSO$_4$ and concentrated to give 3.9 g of crude material. Chromatographic purification on a silica gel column, yielded 1.7 g (77.%) of 3-[1-(2,2-dimethyl-propionyl)-1H-indol-3-yl]-4-(1-methyl-6-nitro-1H-indol-3-yl)-pyrrole-2,5-dione (4) as an orange solid. mp>146° C. with dec. MS: (M$^+$), m/z 470.

F. 3-(1H-Indol-3-yl)-4-(1-methyl-6-nitro-1H-indol-3-yl)-pyrrole-2,5-dione (I)

1.7 g (3.61 mmol) of 3-[1-(2,2-dimethyl-propionyl)-1H-indol-3-yl]-4-(1-methyl-6-nitro-1H-indol-3-yl)-pyrrole-2,5-dione (4) from Step E above in 60 ml of methanol was treated with 5.6 ml (8.96 mmol) of a 1.6 molar solution of NaOCH$_3$ in methanol. The reaction was stirred at room temperature for 1 hour, poured in 2N-HCl/ice and extracted with ethyl acetate. The organic extracts were dried on anhydrous MgSO$_4$ and concentrated to yield, after chromatographic purification, 394.7 mg (28%) of 3-(1H-indol-3-yl)-4-(1-methyl-6-nitro-1H-indol-3-yl)-pyrrole-2,5-dione (I) as a red solid mp>280° C. MS: (M$^+$), m/z 386.

EXAMPLE 2

Preparation of 3-(1-hydroxymethyl-1H-indol-3-yl)-4-(1-methyl-6-nitro-1H -indol-3-yl)-pyrrole-2,5-dione (II)

A. 1-Methoxymethyl-1H-indole (9)

Using the procedure of Example 1, Step A, the N-alkylation reaction of .1.17 g (10 mmol) of commercially available (Aldrich, Milwaukee, Wis.) indole (8) with 1 ml (13.1 mmol) of chloromethyl methyl ether and 0.48 g (12 mmol) of NaH (60% dispersion in oil) as a base in 22 ml of DMF yielded 1.4 g (86.9%) of 1-methoxymethyl-1H-indole (9) as a colorless oil, after chromatographic purification.

B. (1-Methoxymethyl-1H-indol-3-yl)-oxo-acetyl chloride (10)

Using the procedure of Example 1, step B, the reaction of 0.23 g (1.43 mmol) of 1-methoxymethyl-1H-indole (9) from Step A above with 0.25 ml (2.86 mmol) of oxalyl chloride in 3.5 ml of ether produced 0.174 g (48.5%) of (1-methoxymethyl-1H-indol-3-yl)-oxo-acetyl chloride (10) as a yellow solid. This material was used without purification.

C. (6-Nitro-1H-indol-3-yl)-acetonitrile (13)

To a stirred solution of 44.27 g (0.204 mol) of 6-nitrogramine (12) [Jackson B. Hester *J. Org. Chem.*, 29: 1158 (1964)] in 450 ml of acetonitrile 44.59 g (0.31 mol) of methyl iodide was added at 0–5° C. over a period of an hour. The reaction mixture was stirred at room temperature for three hours, then a solution of 26.6 g (0.543 mol) of sodium cyanide in 225 ml of water added at once. The reaction mixture was heated at 32° C. overnight, cooled to room temperature and the product extracted 3 times with a total of 800 ml of ethyl acetate and 300 ml of water. The combined extracts were washed with water, 1N-HCl solution, a saturated sodium bicarbonate solution, dried on MgSO$_4$ and the solvent evaporated in vacuo. The orange-brown residue (41.3 g) was dissolved in 200 ml of warm ethyl acetate and passed through a small pad of silica gel to produce 28.9 g (70.4%) of (6-nitro-1H-indolyl-3-yl)-acetonitrile (13) as a yellow solid after evaporation of the solvent.

D. (1-Methyl-6-nitro-1H-indol-3-yl)-acetonitrile (14)

65.5 g (0.474 mol) of powdered potassium carbonate was added to a solution of 28.9 g (0.143 mol) of (6-nitro-1H-indol-3,yl)-acetonitrile (13) from Step C above in 230 ml of dimethylformamide at room temperature. The suspension was stirred for 40 minutes then 25.48 g (0.179 mol) of methyl iodide was added dropwise over 65 minutes. After stirring at room temperature over night the reaction mixture was cooled and poured into a total of 600 ml of water. The precipitate was filtered, washed with a little water and dried on phosphor anhydride until reaching constant weight. The procedure yielded 30.4 g (95.4%) of (1-methyl-6-nitro-1H-indol-3-yl)acetonitrile (14), which was used without further purification.

E. (1-Methyl-6-nitro-1H-indol-3-yl)-3-ethanimidicacid 1-methylethylester hydrochloride (15)

A stream of HCl gas was bubbled into a stirred suspension of 82 g (0.382 mol) of (1-methyl-6-nitro-1H-indol-3-yl)-acetonitrile (14) from Step D above, in 1000 ml of 2-propanol at 0–10° C. After adding approximately 350 g of HCl, ether was added to the reaction mixture until a precipitate was formed. The solid was collected, washing with ether and dried in vacuo to yield 102 g (85.7%) of (1-methyl-6-nitro-1H-indol-3-yl)-3-ethanimidic acid 1-methylethylester hydrochloride (15).

F. 3-(1-(Methoxymethyl-1H-indol-3-yl)-4-(1-methyl-6-nitro-1H-indol-3-yl)-pyrrole-2,5dione (11)

Using the procedure of Example 1, Step E, the condensation reaction of 1.3 g (5.17 mmol) of oxoacetyl chloride (10) from Step B above, with 1.7 g (5.45 mmol) of (1-methyl-6-nitro-1H-indole)-3-ethanimidic acid 1-methyl ethylester hydrochloride (15) from Step E above in 95 ml of methylene chloride, yielded 1.08 g (48.5%) of 3-(1-methoxymethyl-1H-indol-3-yl)-4-(1-methyl-6-nitro-1H-indol-3-yl)-pyrrole-2,5-dione as an orange solid, mp>250° C. with dec. MS: (M$^+$), m/z 430.

G. 3-(1-Hydroxymethyl-1H-indol-3-yl)-4-(1-methyl-6-nitro-1H-indol-3-yl)-pyrrole-2,5-dione (II)

A solution of 727.5 mg of 3-[1-(methoxymethyl)-1H-indol-3-yl)-4-(1-methyl-6-nitro-1H-indole-3-yl)-pyrrole-2,5-dione (11) from Step F above in 65 ml of THF was treated with approximately 40 ml of 2N-HCl. The reaction mixture was refluxed for 5 hours, cooled and the product was extracted with ethyl acetate. The organic phase was dried on MgSO$_4$ and the solvent evaporated to give an orange solid. Chromatographic purification of this material yielded 123.3 mg of 3-(1-hydroxymethyl-1H-indol-3-yl)-4-(1-methyl-6-nitro-1H-indol-3-yl)-pyrrole-2,5-dione (II) as a red solid, mp 210–213° C. MS: (M$^+$), m/z 416.

EXAMPLE 3 (See Scheme 3)

A. (1-Methyl-1H-indol-3-yl)-oxo-acetyl chloride (17)

Using the procedure of Example 1, Step B, the reaction of 6 ml (47 mmol) of 1-methyl-1H-indole (16) (commercially available from Aldrich, Milwaukee, Wis.) with 8 ml (92 mmol) of oxalyl chloride in 120 ml of ether, produced 7.6 g (73.2%) of (1-methyl-1H-indol-3-yl)-oxo-acetyl chloride (17) as a yellow solid. This material was used without purification.

B. [1-(2,2-Dimethyl-propionyl)-6-nitro-1H-indol-3-yl]-acetonitrile (18)

Using the procedure of Example 1, Step A, the N-alkylation reaction of 346.6 mg (1.72 mmol) of 6-nitro-1H-indolyl-3-acetonitrile (13) from Example 2, Step C with 0.3 ml (2.44 mmol) of trimethylacetyl chloride and 70.8 mg (1.77 mmol) of NaH (60% dispersion in oil) as a base in 8 ml of DMF yielded after chromatographic purification, 287.7 mg (43.2%) of [1-(2,2-dimethyl-propionyl)-6-nitro-1H-indol-3-yl]-acetonitrile (18) as a yellow oil.

C. [1-(2,2-Dimethyl-propionyl)-6-nitro- H-indol-3-yl]-3-ethanimidic acid 1-methylethylester hydrochloride (19)

A stream of HCl gas was bubbled for 3 minutes into a constantly stirred suspension of 1.45 g (5.08 mmol) of 1[-(2,2-dimethyl-propionyl)-6-nitro-1H-indolyl]-3-acetonitrile (18) from Step B above 90 ml of 2-propanol at 0–5° C. The reaction mixture was stirred at room temperature for 21 h. The solvent was evaporated in vacuo to give 1.95 g (100%) of a yellow solid. This material was used without further purification.

D. 3-[1-(2,2-Dimethyl-propionyl)-6-nitro-1H-indol-3-yl]-4-(1-methyl-1H-indol-3-yl)-pyrrole-2,5-dione (20)

Using the procedure of Example 1, Step E, 1.1 g (4.96 mmol) of oxoacetyl chloride (17) from Step A above was reacted with 1.95 g (5.08 mmol) of [1-(2,2-dimethyl-propionyl)-6-nitro-1H-indol-3-yl]-3-ethanimidic acid 1-methylethylester hydrochloride (19) from Step C above and 2.1 ml (17.94 mmol) of triethylamine in 120 ml of methylene chloride, the resulting product was treated with 1.1 g (5.78 mmol) of p-toluenesulfonic acid monohydrate in 80 ml of toluene, yielding 1.3 g (62.1%) of 3-[1-(2,2-dimethyl-propionyl)-6-nitro-1H-indol-3-yl]-4-(1methyl-1H-indol-3-yl)-pyrrole-2,5-dione (20) as an orange solid. mp>245° C. with dec. MS: (M$^+$), m/z 470.

E. 3-(1-Methyl-1H-indol-3-yl)-4-(6-nitro-1H-indol-3-yl)-pyrrole-2,5-dione (III)

Using the procedure of Example 1, Step F, the N-deprotection reaction of 1.3 g (2.76 mmol) of 3-[1-(2,2-dimethyl-propionyl)-6-nitro-1H-indol-3-yl]-4-(1-methyl-1H-indol-3-yl)-pyrrole-2,5-dione (20) from Step D above with 4.3 ml (6.88 mmol) of a 1.6 molar solution of NaOCH3 in 65 ml of methanol yielded 300.6 mg (28.1%) of 3-(1-methyl-1H-indol-3-yl)-4-(6-nitro-1H-indol-3-yl)-pyrrole-2, 5-dione (III) as a red solid after crystallization from ethyl acetate and hexane. mp>260° C. MS: (M$^+$), m/z 386.

EXAMPLE 4

TABLET FORMULATION

| Item | Ingredients | mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

EXAMPLE 5

CAPSULE FORMULATION

| Item | Ingredients | mg/Tablet | | | | |
|---|---|---|---|---|---|---|
| 1 | Compound A* | 5 | 25 | 100 | 250 | 500 |
| 2 | Hydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure
1. Mix Items 1, 2 and 3 in a suitable mixer for 15 minutes.
2. Add Items 4 & 5 and mix for 3 minutes.
3. Fill into a suitable capsule.

EXAMPLE 6

INJECTION SOLUTION/EMULSION PREPARATION

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound represents a compound of the invention.

Manufacturing Procedure
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

EXAMPLE 7

INJECTION SOLUTION/EMULSION PREPARATION

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure
1. Dissolve item 1 in item 2
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 um filter and fill into vials.

What is claimed is:

1. A compound of the formula

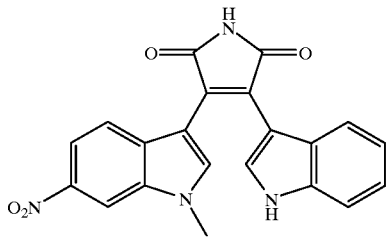

and pharmaceutically acceptable salts of said compound.

2. A compound of the formula

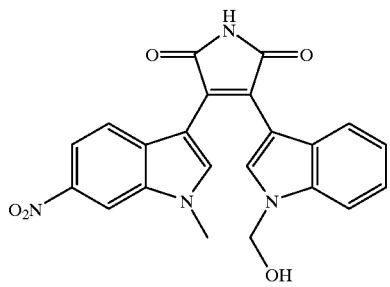

and pharmaceutically acceptable salts of said compound.

3. A pharmaceutical composition comprising a compound of formula

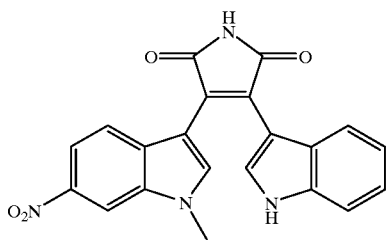

or a pharmaceutically acceptable salt of said compound and a pharmaceutically acceptable carrier.

4. A pharmaceutical composition comprising a compound of formula

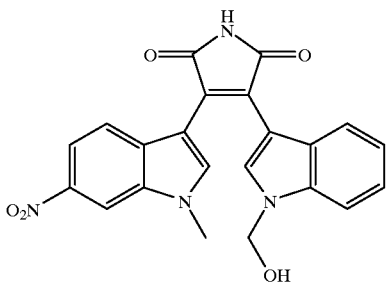

or a pharmaceutically acceptable salt of said compound and a pharmaceutically acceptable carrier.

5. A method for treating solid tumors in a human patient comprising administering to the patient a therapeutically effective amount of compound I or a pharmaceutically acceptable salt of said compound.

6. A method for treating solid tumors in a human patient comprising administering to the patient a therapeutically effective amount of compound II or a pharmaceutically acceptable salt of said compound.

7. The method of claim 5 wherein the therapeutically effective amount of compound I is from about 200 mg to about 5,000 mg per 70 kg patient.

8. The method of claim 6 wherein the therapeutically effective amount of compound II is from about 200 mg to about 5,000 mg per 70 kg patient.

9. An antitumor composition in unit dosage form comprising at least one compound selected from compound I, compound II, and pharmaceutically acceptable salts of said compounds, and a pharmaceutically acceptable carrier, wherein compound I, II, or salt of said compounds is present in an amount of from about 5 mg to about 5,000 mg.

10. The composition of claim 13 wherein compound I, II or salt of said compounds is present in an amount of from about 200 mg to about 1,000 mg.

11. The composition of claim 9 wherein said unit dosage form is a capsule or tablet.

* * * * *

UNITED STATES PATENT AND TRADEMARK OFFICE
CERTIFICATE OF CORRECTION

PATENT NO. : 6,048,887
DATED : April 11, 2000
INVENTOR(S) : Dhingra, et. al.

It is certified that error appears in the above-indentified patent and that said Letters Patent is hereby corrected as shown below:

Claim 10, Column 20, line 41: "[3]" should read ---[9]---.

Signed and Sealed this

Twentieth Day of March, 2001

Attest:

NICHOLAS P. GODICI

Attesting Officer     Acting Director of the United States Patent and Trademark Office